United States Patent
Ruff

(10) Patent No.: US 10,624,945 B2
(45) Date of Patent: Apr. 21, 2020

(54) USE OF AN ALL-D-PENTAPEPTIDE CHEMOKINE ANTAGONIST TO REDUCE OPIOID DOSE IN A PERSON WITH PAIN

(71) Applicant: Creative Bio-Peptides Inc., Potomac, MD (US)

(72) Inventor: Michael R. Ruff, Potomac, MD (US)

(73) Assignee: Creative Bio-Peptides Inc., Potomac, MD (US)

( * ) Notice: Subject to any disclaimer, the term of this patent is extended or adjusted under 35 U.S.C. 154(b) by 0 days.

(21) Appl. No.: 16/177,344

(22) Filed: Oct. 31, 2018

(65) Prior Publication Data

US 2019/0125823 A1 May 2, 2019

Related U.S. Application Data

(60) Provisional application No. 62/579,545, filed on Oct. 31, 2017.

(51) Int. Cl.

| *A61K 38/08* | (2019.01) |
| *A61P 25/04* | (2006.01) |
| *A61K 9/20* | (2006.01) |
| *A61K 9/10* | (2006.01) |

(52) U.S. Cl.
CPC .............. *A61K 38/08* (2013.01); *A61P 25/04* (2018.01); *A61K 9/10* (2013.01)

(58) Field of Classification Search
CPC ............ A61K 38/08; A61K 9/20; A61P 25/04
See application file for complete search history.

(56) References Cited

U.S. PATENT DOCUMENTS

| 5,534,495 | A | * | 7/1996 | Pert | A61K 38/162 |
| | | | | | 514/17.7 |
| 6,011,014 | A | * | 1/2000 | Andersen | A61K 38/08 |
| | | | | | 514/17.9 |
| 10,130,674 | B2 | * | 11/2018 | Pert | A61K 38/08 |
| 2011/0245180 | A1 | * | 10/2011 | Pert | A61K 38/08 |
| | | | | | 514/17.8 |
| 2014/0322250 | A1 | * | 10/2014 | Ruff | C07K 7/08 |
| | | | | | 424/185.1 |
| 2014/0322251 | A1 | * | 10/2014 | Ruff | C07K 7/08 |
| | | | | | 424/185.1 |
| 2014/0323393 | A1 | * | 10/2014 | Ruff | C07K 7/08 |
| | | | | | 514/3.7 |
| 2018/0344798 | A1 | * | 12/2018 | Ruff | A61K 38/08 |
| 2018/0360907 | A1 | * | 12/2018 | Ruff | A61K 38/08 |

OTHER PUBLICATIONS

Stern et al. Drug Delivery: Oral Delivery of Peptides by Petelligence Technology. Drug Development and Delivery. Accessed online at https://drug-dev.com/oral-delivery-of-peptides-by-peptelligence-technology/ on Aug. 5, 2019, 10 pages. (Year: 2013).*

Thermo. Technical Information. "N-Terminal Acetylation and C-Terminal Amidation of Peptides". 2004, 2 pages. (Year: 2004).*

* cited by examiner

*Primary Examiner* — Marcela M Cordero Garcia

(74) *Attorney, Agent, or Firm* — Scott Houtteman; Houtteman Law LLC

(57) ABSTRACT

A method of treatment of pain in a person with a D peptide chemokine receptor antagonist (CRA), and a pharmaceutically acceptable carrier is disclosed. Because chemokines desensitize opiate receptors and enhance the perception of pain said D-peptide CRA, given with a suboptimal dose of an opioid, such as morphine, will restore opioid analgesic efficacy by blocking the cognate chemokine ligand from binding to its receptor and desensitizing the opioid receptor. This strategy of combining a suboptimal dose of morphine with a CRA enhances the potency of morphine, permitting use of lower doses of morphine to obtain equivalent and near maximal analgesia. Lower morphine (opioid) doses have less risk of adverse effects, and potentially also of development of tolerance and dependence.

10 Claims, 3 Drawing Sheets

Specification includes a Sequence Listing.

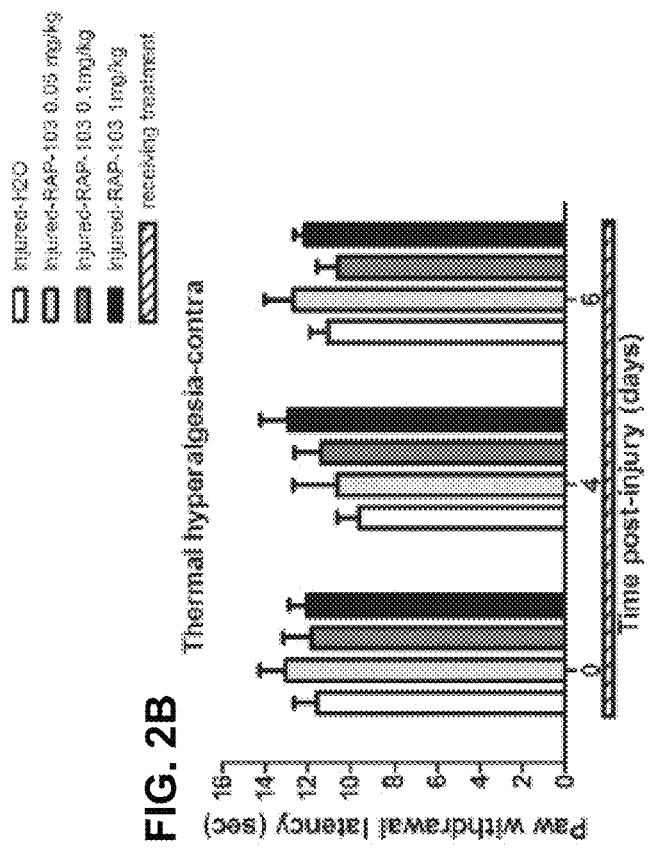
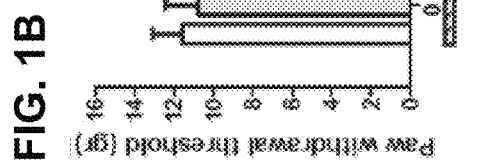
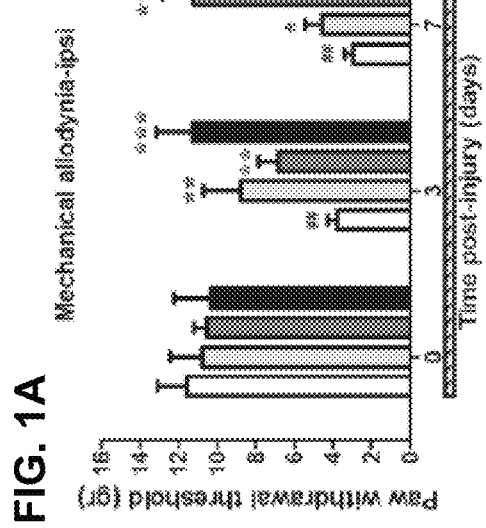
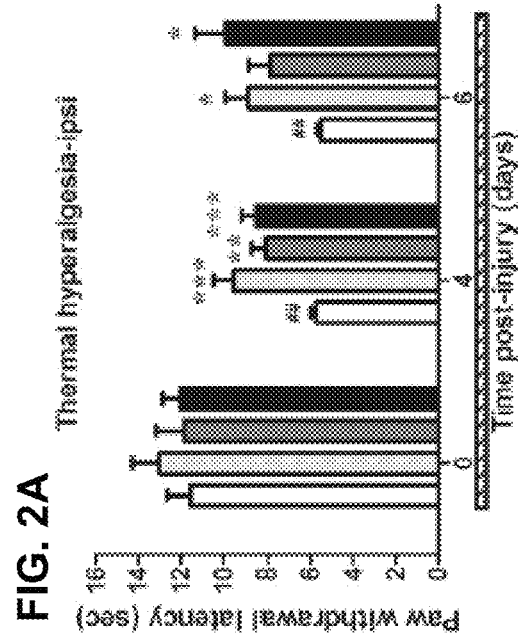

FIG. 3A  CCL2
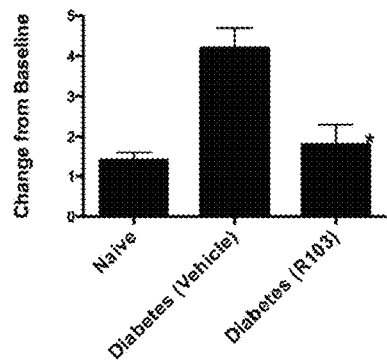
FIG. 3B  CCL3
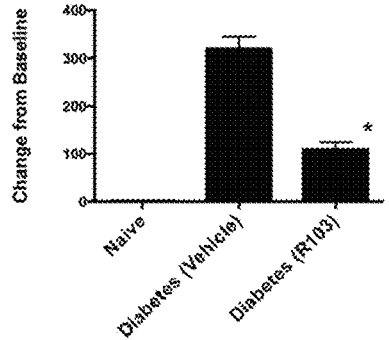
FIG. 3C  CCR2
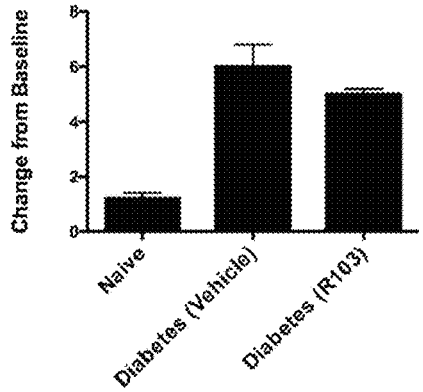
FIG. 3D  CCR5
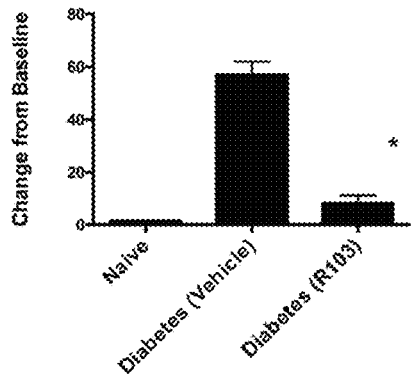
FIG. 3E  IL1β
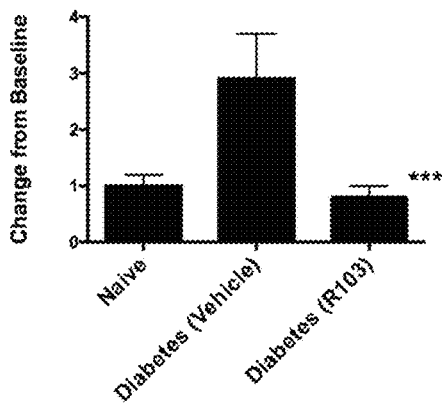
FIG. 3F  TNFα
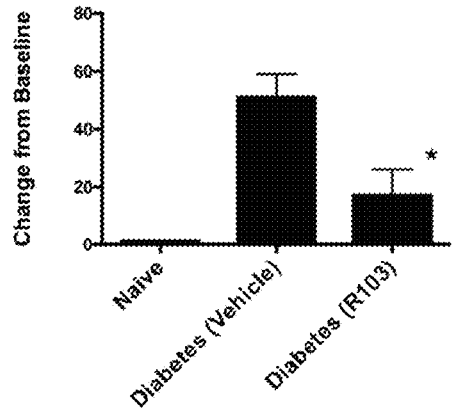

USE OF AN ALL-D-PENTAPEPTIDE CHEMOKINE ANTAGONIST TO REDUCE OPIOID DOSE IN A PERSON WITH PAIN

BACKGROUND

The opioid epidemic is one of the most urgent health emergencies in our country today. Drug overdose is now the leading cause of death for Americans under 50. In 2017, the number of Americans who will die from drug overdose will be roughly the same as the number of Americans who died in the Vietnam, Iraq, and Afghanistan wars combined. Families are at risk due to the parents' addiction. Hundreds of millions of opioid painkillers are given out each year in the U.S. Medically sanctioned opioid prescriptions, such as in post-surgical pain, are often a gateway to addiction. Reduced opioid need would reduce addiction risks.

Severe pain, especially chronic pain, is frequently accompanied by inflammation. Although the most potent and effective drugs are the opioid analgesics, they are accompanied by a number of serious adverse effects, and they are not very effective in approximately half of the cases of chronic pain.

Chemokines desensitize opiate receptors and thereby enhance the perception of pain (Szabo, 2002, Chen, 2007). These findings provide a possible explanation for why opioids are relatively ineffective in inflammatory pain. Chemokines are released during inflammation, and they block the signaling of opioid receptors by a process of heterologous desensitization. From the data above, the hypothesis was formulated that a chemokine receptor antagonist (CRA), given with a suboptimal dose of morphine, will restore opioid analgesic efficacy by blocking the cognate chemokine ligand from binding to its receptor and desensitizing the opioid receptor.

Because opioids are used in the management of diabetic neuropathic pain (Patil, 2015). we determined the efficacy of a small peptide chemokine receptor antagonist RAP-103 (all-D-TTNYT) to block pain in a model of diabetic neuropathy.

Painful diabetic neuropathy (PDN) is a common complication of diabetes which adversely affects patients' daily life and represents a major public health problem. Although this painful signal is believed to originate in the peripheral nervous system, the precise cellular mechanisms of chronic pain associated with PDN remain poorly understood. Inspired by the critical contribution of inflammation in injury models of neuropathic pain, here we reasoned that if inflammation is also engaged in the pathogenesis of diabetic neuropathic pain, then 1) infiltration of immune cells in damaged nerves and/or activation of spinal microglia should coincide with the development of pain; 2) inhibiting inflammatory response in the peripheral and/or the central nervous system should reduce chronic pain. To test the hypothesis, we first used behavioral and molecular/cellular approaches to explore chronic pain development and inflammatory reaction in Streptozotocin (STZ) induced diabetic rats. Our results showed that following the induction of diabetes, rats exhibited persistent mechanical and cold allodynia (up to five months post-induction). The levels of inflammatory molecules, including cytokines, IL1β, TNFα; chemokines CCL2, CCL3; and chemokines receptors CCR2 and CCR5 were dramatically increased in sciatic nerves and RAP-103 lowered them (FIG. 3). Microglia in the spinal cord dorsal horns became activated with hypertrophic morphology and an increase in microglial cell number. CCL2 and CCL3 are two chemokines well known in mediating immune cell trafficking and immune response in the context of neuropathic pain. Oral administration of RAP-103, a CCR2/CCR5 dual receptor antagonist for 7 days inhibited PDN associated inflammation by reducing significantly all examined inflammatory mediators. The effect of RAP-103 is more pronounced at peripheral nerves.

BRIEF DESCRIPTION OF THE FIGURES

FIGS. 1A-B. RAP103 reversed mechanical allodynia in rats with neuropathic pain.

FIGS. 2A-B. RAP103 reversed cold allodynia in rats with neuropathic pain.

FIGS. 3A-F. RAP103 (0.5 mg/kg, for 7 days, p.o.) significantly inhibited inflammation in the sciatic nerves of STZ rats FIG. 4. RAP103 potentiates morphine analgesia in an animal model of post-surgical pain.

Figure 4:
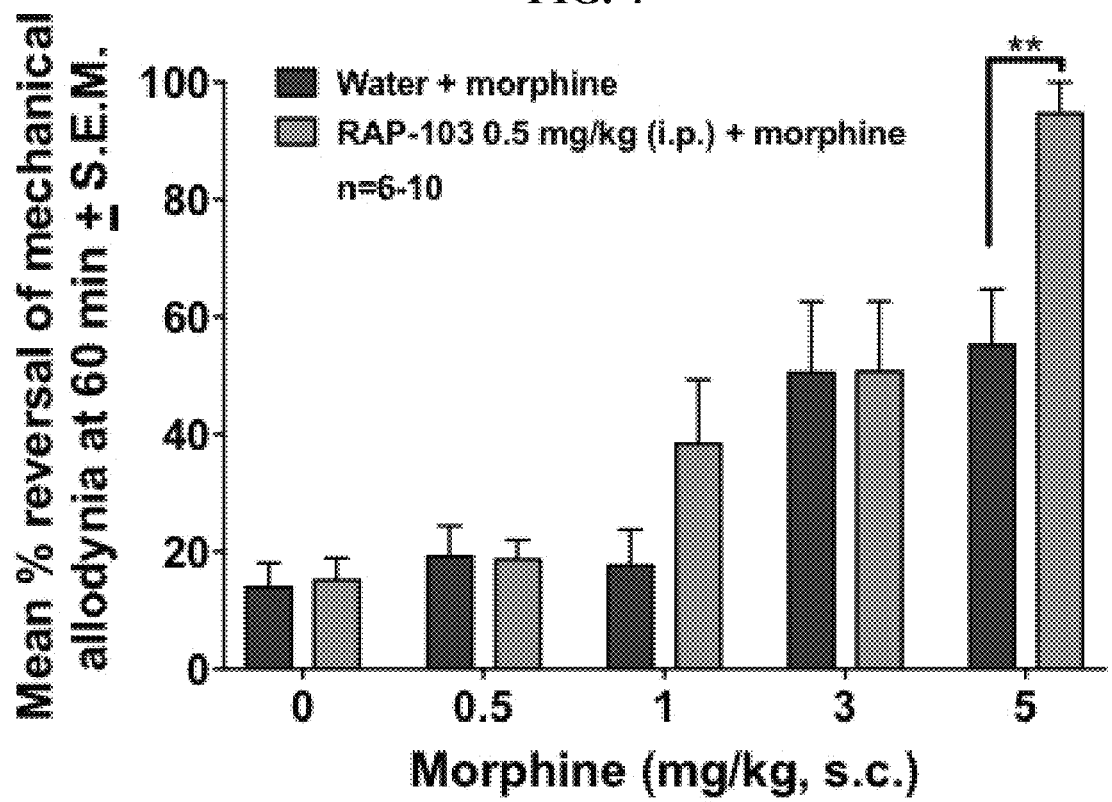

The treatment with RAP-103 (also referred to as R103) (0.5.-0.02 mg/Kg b.w., daily, for 7 days, resulted in a complete reversal of established hypersensitivity in STZ rats. The results suggest that functional antagonism of multiple chemokine receptors and innate immune receptors may be treatments and medicines for pain and inflammation. In view of the results showing that chemokines reduce opioid efficacy, these results suggest that administration of a chemokine receptor antagonist, like R103 (all-D-TTNYT), or related all-D-pentapeptides of the list below, will reduce pain by any cause, but especially inflammatory pain, to include back pain, post-surgical pain, neuropathic pain, cancer pain, pain from injury or trauma etc., and can reduce the amount or duration of opioid use in a person in need of pain control. The effective human doses suggested by these animal studies would be 0.01 to 2 mg/Kg/day. The peptides may be dosed as an oral pill, suspension, liquid, or by IV and subcutaneous injections to achieve pain control with decreased concomitant opioid use. Some examples of other useful CRA antagonists that can reduce opioid dose or use are Maraviroc (a CCR5 antagonist) or AMD3100 (a CXCR4 antagonist).

Materials and Methods

Induction and assessment of diabetes in rats Rats were fasted overnight and received a single intraperitoneal injection of streptozotocin (60 mg/kg, Sigma-Aldrich) in citrate buffer (pH 4.5) to induce type I diabetes. The induction of diabetes was confirmed 72 h after streptozotocin injection by measurement of blood glucose levels using Contour® blood glucose diagnostic kit (Bayer HealthCare, Canada). Body weight and blood glucose levels were measured before and 3 days after streptozotocin injection, once a week for three weeks after diabetes induction. Only rats having blood glucose concentration consistently higher than 300 mg/dl were used for the present study.

Drug Preparations:

The drug was prepared by dissolving 5 mg RAP103 in 50 ml autoclaved $H_2O$ at room temperature, which made up an initial concentration at 0.1 mg/ml. This source drug solution was prepared freshly for each experiment and it was kept for 8 days (duration of one experiment) at room temperature. Appropriate concentration for each dose was adjusted accordingly.

Treatment Paradigms

To investigate whether R103 (all-D-TTNYT), a drug which acts directly on CCR5 and CCR3 chemokine receptors can reverse already established neuropathic hypersensitivity in diabetic rats, autoclaved water or R103 (0.004, 0.02, 0.1 or 0.5 mg/kg b.w.) was administered daily by oral gavage to rats who exhibited stable mechanical and cold allodynia. The treatment lasted for 8 days (n=5 for H$_2$O and n=7 for RAP-103/each dose).

Assessment of Pain Sensitivity

Tactile Allodynia

Mechanical sensitivity was assessed using calibrated von Frey hairs as described by Chaplan et al (1994). Animals were placed in Plexiglas boxes on an elevated metal mesh floor and allowed 60 min for habituation before testing. A series of von Frey filaments with logarithmically incrementing stiffness (Stoelting) was applied perpendicular to the mid-plantar region of the hind paw. The 50% paw withdrawal threshold was determined using Dixon's up-down method as previously described (Dixon, 1980). Withdrawal thresholds of both paws were averaged as one single value per animal.

Cold Allodynia

The same apparatus (Plexiglas cylinder resting on a mesh floor) as the one described above for the von Frey test was used. Rats were allowed adapting to the testing environment for at least 10 min. Then, a drop (50 μl) of acetone was applied with a glass syringe fitted with a blunted needle at the center of the plantar face of a hind paw. Acetone was applied alternately twice to each hind paw, with 5 min between each successive application. Responses were monitored during 1 min after acetone application and were graded according to a 4-point scale, as previously described by Flatters and Bennett (2004): 0, no response; 1, quick withdrawal, flick or stamp of the paw; 2, prolonged withdrawal or repeated flicking of the paw; 3, repeated flicking of the paw with persistent licking directed at the ventral side of the paw. Cumulative scores were then obtained by summing the four scores for each rat, the minimum score being 0 (no response to any of the four trials) and the maximum possible score being 12 (repeated flicking and licking of paws on each of the four trials).

Rats were habituated to the testing environment daily for at least two days before the experiments started. All animals were assessed for mechanical allodynia and cold allodynia of both hind paws before (behavioral baseline values before STZ injection) and once a week after diabetes induction until they exhibited stable hypersensitive states (before RAP103 treatment), where the treatment with RAP103 started. Assessment on the effects of RAP103 on mechanical and cold allodynia was performed between 2-4 hours following the drug administration.

Data Analysis

All data were presented as means±SEM. Statistical analysis was performed by two-way ANOVA followed by Bonferroni post-tests. The criterion for statistical significance was P<0.05.

Use of R103 to Reduce the Need for Opioids in the Treatment of Pain

Animals:

Male, Sprague-Dawley rats (210-250 g) were purchased from Taconic Biosciences and acclimated in the animal house for a week before initiation of experiments. At the beginning of testing, 2 days prior to surgery, rats were placed into individual transparent cubicles with a wire mesh floor for an hour a day, to acclimate them to the testing chambers.

Surgery:

On the day of surgery, rats were acclimated for 30 min in the chambers, and then their individual baseline values for mechanical allodynia were assessed. Paw withdrawal thresholds were measured using a series of von Frey filaments (North Coast Medical, Inc., Gilroy, Calif.), with gradually increasing logarithmic bending forces (equivalent to 2, 4, 6, 8, 10, 15, 26, and 60 g force). The filaments were applied to the plantar side of each hind paw in an ascending matter. Each filament was tested five consecutive times a few seconds apart. A positive response was defined as quick withdrawal or paw flinching after the application of a filament. Surgery was performed under isoflurane anesthesia (4% isoflurane for induction and 2.5% isoflurane for maintenance of anesthesia) using aseptic conditions. A 1 cm longitudinal incision (starting 0.5 cm from proximal edge of the heel and extending toward the toes) was made with a scalpel through skin and the fascia of the plantar side of the left hind paw. The plantaris muscle was exposed, elevated and incised longitudinally. Following bleeding control with gentle pressure, the skin was closed with two single interrupted sutures using 5-0 nylon. Animals were brought back to their individual chambers for mechanical allodynia testing. For kinetic assessment of pain, the time of surgery completion was designated as time 0. Paw withdrawal thresholds were recorded by a person blinded to the treatments at time points of 15, 30, 45, 60, 120, 240, and 360 min on the day of surgery, as well as 24, 48, and 72 h after surgery.

Treatment:

The compound, RAP-103, a CCR2/CCR5/CCR8 antagonist was tested for analgesic capacity. RAP-103 was supplied as a powder, and was reconstituted in sterile, pyrogen-free water. Solutions were prepared and kept frozen until use. On the day of the experiment, solutions were thawed and kept on ice until they were injected into rats. Rats were injected i.p., 25 min post-surgery. Control animals received water (vehicle). Morphine sulfate was dissolved in pyrogen-free saline and injected s.c. in the dorsal flank at 25 min post-surgery.

Co-Administration of RAP-103 with Morphine

In this experiment, RAP-103 at a single dose, 0.5 mg/kg, was combined with morphine (0.5 to 5.0 mg/kg) and the percent reversal of mechanical allodynia was compared to that of morphine alone at the different doses. The range of doses for morphine were previously established in our laboratory in this assay. FIG. 4 shows that when 5.0 mg/kg of morphine was compared to the same dose of morphine plus 0.5 mg/kg of RAP-103, statistically significantly greater analgesia was observed in animals receiving the combination treatment, than in rats receiving morphine alone.

Dose Response Curves of Morphine Alone Compared to Morphine Plus RAP-103

A comparison of morphine alone at different doses with morphine plus RAP-103 was tested in the incisional pain assay. Percent reversal of mechanical allodynia was calculated using data from t=60 min. % reversal=[(60 min threshold−predose threshold)/(baseline threshold−predose threshold)]×100. Data were analyzed by two-way ANOVA followed by Sidak's multiple comparison test, **p<0.01.

Figure 5:
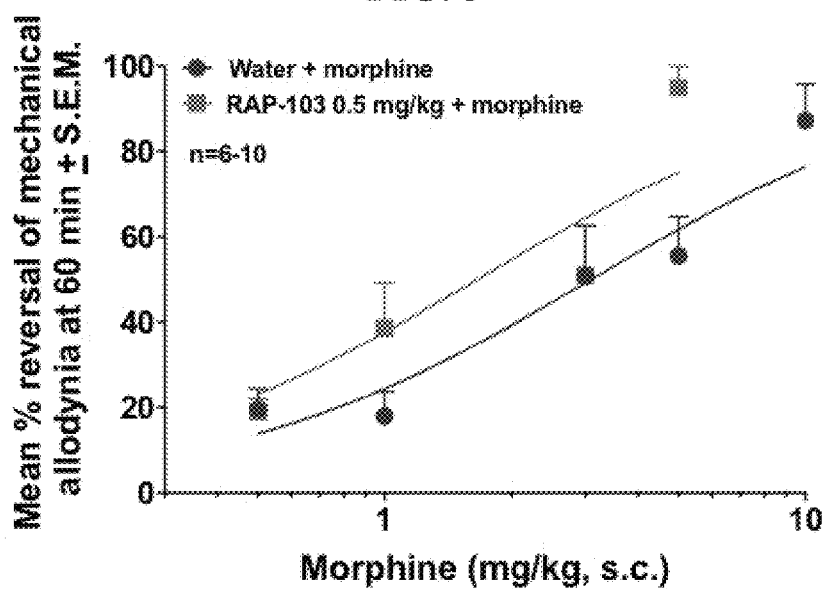
FIG. 5. Dose response curves of morphine alone compared to morphine plus RAP-103.

In FIG. 5 dose response curves are shown for morphine alone and for morphine plus RAP-103 (0.5 mg/kg) for ability to reverse mechanical allodynia, a measure of pain sensitivity. The ED$_{50}$ values were calculated from the graphic dose-response curves. As shown, the ED$_{50}$ for morphine was shifted to the left by about 2-fold by the addition of RAP-103. The ability of RAP-103 to potentiate opioid efficacy suggests further uses of RAP-103, and the related peptides of the invention, to be novel treatments for addictions in general, and opioid use disorders in particular.

Szabo, I., et al., *Heterologous desensitization of opioid receptors by chemokines inhibits chemotaxis and enhances the perception of pain.* Proc Natl Acad Sci USA, 2002. 99(16): p. 10276-81.

Chen, X., et al., *Rapid heterologous desensitization of antinociceptive activity between mu or delta opioid receptors and chemokine receptors in rats.* Drug Alcohol Depend, 2007. 88(1): p. 36-41.

Patil, P. R., et al., *Opioid use in the management of diabetic peripheral neuropathy (DPN) in a large commercially insured population.* Clin J Pain, 2015. 31(5): p. 414-24.

What is claimed is:

1. A method of reducing the effective amount or duration of opioid in a patient using said opioids to manage pain comprising the steps of: preparing a chemokine receptor antagonist pharmaceutical composition comprising an all-D peptide and a pharmaceutically acceptable carrier, said peptide comprises five contiguous amino acids and is at most 8 amino acid residues in length, having the general structure: A-B-C-D-E in which:

A is Ser, Thr, Asn, Glu, Ile,

B is Ser, Thr, Asp, Asn,

C is Thr, Ser, Asn, Arg, Trp,

D is Tyr, and

E is Thr, Ser, Arg, Gly, all amino acids being the D stereoisomeric configuration and, administering said composition to the patient in a therapeutically effective dose, wherein said composition acts to manage pain and reduce the effective amount or duration of opioid use in the patient.

2. The method as defined in claim 1 wherein said D peptide is TTNYT (SEQ ID NO: 1).

3. The method as defined in claim 1 wherein the D peptide has a sequence selected from the group consisting of:

```
                                          (SEQ ID NO: 1)
         Thr Thr Asn Tyr Thr, (SEQ ID NO: 2)
         Ser Ser Thr Tyr Arg, (SEQ ID NO: 3)
         Ser Thr Asn Tyr Thr, (SEQ ID NO: 4)
         Thr Thr Ser Tyr Thr, (SEQ ID NO: 5)
         Asn Thr Ser Tyr Gly, (SEQ ID NO: 6)
         Glu Thr Trp Tyr Ser (SEQ ID NO: 7)
         Asn Thr Ser Tyr Arg (SEQ ID NO: 8)
         Ile Asn Asn Tyr Thr, (SEQ ID NO: 9)
         Ile Asp Asn Tyr Thr (SEQ ID NO: 10)
         Thr Asp Asn Tyr Thr (SEQ ID NO: 11)
         Thr Asp Ser Tyr Ser (SEQ ID NO: 12)
         Thr Asn Ser Tyr Arg (SEQ ID NO: 13)
         Asn Thr Arg Tyr Arg.
```

4. The method as defined in claim 1 wherein E is esterified, glycosylated, or amidated to enhance tissue distribution.

5. The method as defined in claim 1 wherein said composition is used as an oral pill having between 0.5 to 100 mgs of the peptide.

6. The method as defined in claim 1 wherein said composition is used as an oral pill having between 0.1 to 500 mgs of the peptide.

7. The method as defined in claim 1 wherein said chemokine receptor antagonist reduces the effective amount of opioid use by the patient.

8. The method as defined in claim 1 wherein said chemokine receptor antagonist is Dala1-peptide T-amide (DAPTA).

9. The method as defined in claim 1 wherein said chemokine receptor antagonist is Dala1-peptide T-amide (DAPTA) and is used to reduce the effective amount of opioid used by need for opioid used by the patient.

10. A method of pain treatment as defined in claim 1 wherein said chemokine receptor antagonist is administered as a pill or liquid.

\* \* \* \* \*

```
                          SEQUENCE LISTING

<160> NUMBER OF SEQ ID NOS: 13

<210> SEQ ID NO 1
<211> LENGTH: 5
<212> TYPE: PRT
<213> ORGANISM: Human immunodeficiency virus

<400> SEQUENCE: 1

Thr Thr Asn Tyr Thr
1               5

<210> SEQ ID NO 2
<211> LENGTH: 5
<212> TYPE: PRT
<213> ORGANISM: Human immunodeficiency virus

<400> SEQUENCE: 2

Ser Ser Thr Tyr Arg
1               5

<210> SEQ ID NO 3
<211> LENGTH: 5
<212> TYPE: PRT
<213> ORGANISM: Human immunodeficiency virus

<400> SEQUENCE: 3

Ser Thr Asn Tyr Thr
1               5

<210> SEQ ID NO 4
<211> LENGTH: 5
<212> TYPE: PRT
<213> ORGANISM: Human immunodeficiency virus

<400> SEQUENCE: 4

Thr Thr Ser Tyr Thr
1               5

<210> SEQ ID NO 5
<211> LENGTH: 5
<212> TYPE: PRT
<213> ORGANISM: Human immunodeficiency virus

<400> SEQUENCE: 5

Asn Thr Ser Tyr Gly
1               5

<210> SEQ ID NO 6
<211> LENGTH: 5
<212> TYPE: PRT
<213> ORGANISM: Human immunodeficiency virus

<400> SEQUENCE: 6

Glu Thr Trp Tyr Ser
1               5

<210> SEQ ID NO 7
<211> LENGTH: 5
```

```
<212> TYPE: PRT
<213> ORGANISM: Human immunodeficiency virus

<400> SEQUENCE: 7

Asn Thr Ser Tyr Arg
1               5

<210> SEQ ID NO 8
<211> LENGTH: 5
<212> TYPE: PRT
<213> ORGANISM: Human immunodeficiency virus

<400> SEQUENCE: 8

Ile Asn Asn Tyr Thr
1               5

<210> SEQ ID NO 9
<211> LENGTH: 5
<212> TYPE: PRT
<213> ORGANISM: Human immunodeficiency virus

<400> SEQUENCE: 9

Ile Asp Asn Tyr Thr
1               5

<210> SEQ ID NO 10
<211> LENGTH: 5
<212> TYPE: PRT
<213> ORGANISM: Human immunodeficiency virus

<400> SEQUENCE: 10

Thr Asp Asn Tyr Thr
1               5

<210> SEQ ID NO 11
<211> LENGTH: 5
<212> TYPE: PRT
<213> ORGANISM: Human immunodeficiency virus

<400> SEQUENCE: 11

Thr Asp Ser Tyr Ser
1               5

<210> SEQ ID NO 12
<211> LENGTH: 5
<212> TYPE: PRT
<213> ORGANISM: Human immunodeficiency virus

<400> SEQUENCE: 12

Thr Asn Ser Tyr Arg
1               5

<210> SEQ ID NO 13
<211> LENGTH: 5
<212> TYPE: PRT
<213> ORGANISM: Human immunodeficiency virus

<400> SEQUENCE: 13

Asn Thr Arg Tyr Arg
1               5
```